United States Patent [19]

Jeram

[11] 4,072,635
[45] Feb. 7, 1978

[54] ORGANOSILOXANE GELS

[75] Inventor: Edward M. Jeram, Burnt Hills, N.Y.

[73] Assignee: General Electric Company, Waterford, N.Y.

[21] Appl. No.: 584,392

[22] Filed: June 6, 1975

Related U.S. Application Data

[63] Continuation-in-part of Ser. No. 160,162, July 6, 1971, abandoned.

[51] Int. Cl.$^2$ ............................................. C08J 9/32
[52] U.S. Cl. ............................. 260/2.5 S; 260/2.5 B; 260/375 B; 260/46.5 UA; 260/46.5 G; 160/46.5 H
[58] Field of Search ................. 260/46.5 UA, 46.5 G, 260/825, 375 B, 2.5 B, 46.5 H

[56] References Cited

U.S. PATENT DOCUMENTS

| | | | |
|---|---|---|---|
| 2,797,201 | 6/1957 | Veatch et al. | 260/2.5 B |
| 2,806,509 | 9/1957 | Bozzacco et al. | 260/2.5 B |
| 2,978,340 | 4/1961 | Veatch et al. | 260/2.5 B |
| 3,020,260 | 2/1962 | Nelson | 260/46.5 R |
| 3,317,455 | 5/1967 | Blome et al. | 260/37 S B |
| 3,548,420 | 12/1970 | Spence | 260/46.5 H |
| 3,926,581 | 2/1976 | Gorden | 260/46.5 UA |
| 3,928,629 | 12/1975 | Chandra et al. | 260/46.5 UA |
| 3,950,300 | 4/1976 | Hittmair et al. | 260/46.5 UA |

Primary Examiner—Morton Foelak
Attorney, Agent, or Firm—E. Philip Koltos; Donald J. Voss; Frank L. Neuhauser

[57] ABSTRACT

An organosiloxane gel is made by reacting (1) an organosiloxane having a viscosity of from 10 to 10,000 centistokes at 25° C and being a copolymer consisting essentially of units of the formula $R_2ViSiO_{0.5}$, $RViSiO$, $R_2SiO$ and $MeR_2SiO_{0.5}$, where each R is individually selected from the group consisting of methyl and phenyl radicals, Vi represents a vinyl radical and Me represents a methyl radical, at least 0.50 molar percent of the units in said copolymer being $R_2ViSiO_{0.5}$ units and $RViSiO$ units where the terminal groups are at least 50 mole percent of $R_2ViSiO_{0.5}$ units and may have as the rest of the total terminal units $MeR_2SiO_{0.5}$ units, (2) a liquid hydrogen siloxane of the average general formula $XRMeSiO(R_2SiO)_n(RHSiO)_mSiMeRX$, where each R is as above defined and X is selected from the group consisting of H and R and n and m have such average values that the viscosity of the hydrogen siloxane is no more than 10,000 centistokes at 25° C and m is at least 1, no more than 25 molar percent of the total R radicals present in (1) and (2) being phenyl and (3) a platinum or platinum compound catalyst in an amount sufficient to furnish about at least 0.1 part per million of platinum based upon the combined weights of (1) and (2); the proportions of (1) and (2) being such that prior to reaction there is an average of from 1.4 to 1.8 gram atoms of the silicon-bonded hydrogen atoms in (2) per gram molecular weight of (1) and there being at least one vinyl siloxy units in (1) for every silicon-bonded hydrogen atom in (2), the molecular weight of (1) being calculated by the equation:

$$\log \text{visc.} = 1.00 + 0.0123 M^{.5}$$

where M is the molecular weight and "visc." is the viscosity of (1) in centistokes at 25° C. The gel can be filled with glass microballoons to lower their specific gravity. The gel produced finds utility in collision pads in automobiles, shock absorbing bumpers, mattresses, snowmobile seats, padding and crash helmets and insulation which can be pumped into electrical conduits, among other things.

18 Claims, No Drawings

ORGANOSILOXANE GELS

The present application is a continuation-in-part of parent patent application Ser. No. 160,162, filed July 6, 1971, now abandoned.

BACKGROUND OF THE INVENTION

The present invention is directed to silicone gels which are neither a solid nor a liquid. The gels can be flowing or non-flowing but can be made to flow if sufficient pressure is applied. Silicone gels are known in the art having been described in U.S. Pat. No. 3,020,260 of Nelson and 3,308,491 of Spence.

While the silicone gel compositions presently available are quite useful as electrical encapsulating materials and as orthopedic gel pads used to prevent bed sores, they are somewhat lacking in processability. What is needed is a gel which can be cured in 10 seconds on an electronic encapsulating line and a gel which has a pot life of at least 16 hours for use in making orthopedic gel pads. The long pot life would allow the gel to be used to fill some orthopedic pads and then the unused stored for an overnight period and used the next morning to fill additional pads without the problem of the material curing during storage.

SUMMARY OF THE INVENTION

The present invention is based upon the discovery that vinyl-terminated polysiloxanes containing in-chain vinyl groups provide the unusually fast cure times necessary for mass production of encapsulated electronic components. By varying only the hydrogen containing component of the gel and using the same vinyl containing polymer, large variations in cure time and pot life can be achieved.

An additional element of the present invention is the use of plastic or glass microballoons as filler. The microballoons are preferably made of glass but can also be made from urea formaldehyde, phenolic or other plastic, even fly ash to decrease the density of the gel pads. The specific gravity of a gel pad not containing low density fillers such as microballoons is in the neighborhood of one. The specific gravity can easily be cut down by at least a factor of one-third if microballoon fillers are used. This allows the pads to be more easily handled when used on hospital beds, hotel beds, etc. It also provides for a decrease in the weight of encapsulated airborne electronic equipment.

DESCRIPTION OF THE PREFERRED EMBODIMENTS

The organopolysiloxane gel of the present invention is a reaction product of a mixture consisting essentially of (1) an organosiloxane having a viscosity of from 10 to 10,000 centistokes at 25° C and being a copolymer consisting essentially of units of the formula $R_2ViSiO_{0.5}$, $R_2SiO$, $RViSiO$ and $MeR_2SiO_{0.5}$, where each R is individually selected from the group consisting of methyl and phenyl radicals and Vi represents a vinyl radical, at least 0.50 molar percent of the units in said copolymer being $R_2ViSiO_{0.5}$ units and RViSiO units where the terminal groups are at least 50 mole percent of $R_2ViSiO_{0.5}$ units and may have as the rest of the total terminal units $MeR_2SiO_{0.5}$ units, (2) a liquid hydrogensiloxane of the average general formula, $XRMeSiO(R_2SiO)_n$—(RHSiO)$_m$SiMeRX, where each R is as above defined and X is selected from the group consisting of H and R, no more than 25 molar percent of the total R radicals present in (1) and (2) being phenyl, and $n$ and $m$ have such average values that the viscosity of the hydrogensiloxane is no more than 10,000 centistokes at 25° C and $m$ is at least 1, and (3) a platinum or platinum compound catalyst in an amount sufficient to furnish at least 0.1 part per million of platinum based upon the combined weights of (1) and (2); the properties of (1) and (2) being such that prior to reaction there is an average of from 1.4 to 1.8 gram atoms of the silicon-bonded hydrogen atoms in (2) per gram molecular weight of (1) and there being at least one vinyl siloxy unit in (1) for every silicon-bonded hydrogen atom in (2), the molecular weight of (1) being calculated by the equation:

$$\log \text{visc.} = -1.00 + 0.0123 M^{.5}$$

where M is the molecular weight and "visc." is the viscosity of (1) in centistokes at 25° C.

The organosiloxane copolymers defined as constituent (1) above are well-known materials. They can be prepared, for example, by the cohydrolysis and cocondensation of the corresponding halosilanes, i.e., $R_2ViSiCl$, $RViSiCl_2$, $R_2SiCl_2$ and $CH_3R_2SiCl$ or by the copolymerization and equilibration of the corresponding siloxanes. Thus, for example, siloxanes of the formulas $(RViSiO)_4$, $(R_2SiO)_4$ and $(ViR_2Si)_2O$ can be mixed in appropriate ratios and heated at 150° to 160° C in the presence of a catalyst such as NaOH, KOH, LiOH until an equilibrium is established, then the copolymer neutralized with $H_3PO_4$. It is preferred that the copolymer used in this invention be substantially free of silicon-bonded hydroxy groups.

The R radicals in the above-defined copolymer can be the same or different radicals in each polymeric unit or in the molecule. Thus, the copolymer can contain the units MeViSiO, PhViSiO, $Me_2SiO$, $Ph_2SiO$, $Me_2ViSiO_{0.5}$, $Ph_2ViSiO$, $Me_3SiO_{0.5}$, $ViMePhSiO_{0.5}$ and PhMeSiO in any combination so long as the viscosity and vinyl content requirements are met and the phenyl content does not exceed 25 molar percent. The symbols Me, Ph and Vi are used here and throughout the specification as representative of methyl, phenyl and vinyl radicals respectively.

The copolymer (1) should have a viscosity of from 10 to 10,000 centistokes at 25° C. This is, of course, controlled by the amount of the endblocking $ViR_2SiO_{0.5}$ units present as well as any $MeR_2SiO_{0.5}$ units that may be present. It must be specified that in copolymer (1) the amount of $ViR_2SiO_{0.5}$ terminal units may be as low as 50 mole percent of total terminal units present with the rest being $MeR_2SiO_{0.5}$ and the amount of $ViR_2SiO_{0.5}$ units may be as high as 100 mole percent of the total terminal units present. Preferably, the amount of $ViR_2SiO_{0.5}$ units present is between 80 to 100 mole percent of the terminal units present. Preferably, this copolymer is substantially free of volatile low molecular weight species. As is well known, however, material of any particular viscosity will itself be composed of innumberable species of molecules having different molecular weights, and it is the viscosity of the mixture of species which is important here. Viscosities of from about 400 to 1000 centistokes are preferred.

The hydrogensiloxane (2) employed herein has the average general formula $XRCH_3SiO(R_2SiO)_n(RHSiO)_m SiMeRX$, where each R is methyl or phenyl, X is R or H, $n$ is 0 or any positive integer or fraction so long as the viscosity does not exceed 10,000 centistokes at 15°

C, m is at least 1 and any positive integer or fraction so long as the viscosity does not exceed 10,000 centistokes at 25° C, thus the sum of m + n can vary from 1 to 1,000 inclusive, the upper limit, of course, varying with the type of R and X radicals present. Viscosities in the range of from 1 to 1000 centistokes are most preferred. The R radicals in a given molecule or in a given mixture of molecular species falling within this definition can be the same or different radicals. Thus, the endblocking units can be $HMe_2SiO_{0.5}$ units and/or $HMePhSiO_{0.5}$ units, and/or $Me_3SiO_{0.5}$ units. Repeating units present can be $Me_2SiO$, $MePhSiO$, $Ph_2SiO$ units and must contain $MeHSiO$ units or any combination of these endblocking and repeating units can be used. However, when phenyl radicals are present in either constituent (1) or constituent (2) as defined herein, the total number of such phenyl radicals should not exceed 25 molar percent of the total R radicals present in (1) plus (2), with a preferred maximum being about 10 molar percent.

The defined hydrogensiloxanes are known compounds and can be prepared, e.g., by the cohydrolysis and cocondensation of the corresponding chlorosilanes, i.e., $MeRSiHCl$, $MeSiHCl_2$, $RMe_2SiCl$, $RSiHCl_2$ and $R_2SiCl_2$, or by the acid catalyzed equilibration of the siloxanes $(MeRHSi)_2O$, $(RMe_2Si)_2O$, $(R_2SiO)_4$, and $(RHSiO)_4$.

The production of the gel requires the control of the proportions of the siloxanes (1) and (2) employed. The proportions are such that prior to reaction there is an average of from 1.4 to 1.8 inclusive (preferably 1.45 to 1.7) of the silicon-bonded H atoms in (2) per molecule of (1), with there being at least one vinyl substituted siloxy unit in (1) for each such H atom, when the molecular weight of (1) has been calculated by the equation:

$$\log \text{visc. (cs. at } 25°\text{ C)} = 1.00 + 0.0123 M^{.5}$$

The amount of "SiH" present in (2) is preferably determined by the known analytical methods for such determinations, although it too can be calculated from the viscosity of (2).

It can be seen that the weight ratios of (1) and (2) are thus subject to extremely wide variations, for they are dependent entirely upon the molecular weight of the one and the SiH content of the other. The equation used for determining the molecular weight of (1) gives a "number average" molecular weight, and has been shown by A. J. Barry to be reasonably valid for linear methylpolysiloxane fluids having molecular weights above 2500 (Journal of Applied Physics, vol. 17, 1020–1024, December 1946). Of course, the expression may not be exactly accurate, particularly when phenyl radicals or a relatively large amount of vinyl radicals are present. Nevertheless, the calculation of molecular weight in this manner when used in conjunction with the defined limitations does express the proportions of (1) and (2) required for the desired results.

The gels of this invention are formed when the defined proportions of (1) and (2) are intimately mixed with a catalyst, preferably a platinum compound catalyst and allowed to react. Many types of platinum compound catalysts for the SiH-olefin addition reaction are known, but the preferred forms especially when optical clarity is required are those platinum compound catalysts which are soluble in the reaction mixture. The platinum compound can be selected from those having the formula $(PtCl_2.\text{olefin})_2$ and $H(PtCl_3.\text{olefin})$, as described in U.S. Pat. No. 3,156,601—Ashby. The olefin shown in the previous two formulas can be almost any type of olefin, but is preferably an alkene having from 2 to 8 carbon atoms, a cycloalkene having from 5 to 7 carbon atoms or styrene. Specific olefins utilizable in the above formulas are ethylene, propylene, the various isomers of butylene, octylene, cyclopentene, cyclohexene, cycloheptene, etc. A further platinum-containing material usable in the composition of the present invention is the platinum chloride cyclopropane complex $(PtCl_2.C_3H_6)_2$ described in U.S. Pat. No. 3,159,662 — Ashby.

Still further, the platinum-containing material can be a complex formed from chloroplatinic acid with up to 2 moles per gram of platinum of a member selected from the class consisting of alcohols, ethers, aldehydes and mixtures of the above as described in U.S. Pat. No. 3,220,972—Lamoreaux.

The preferred platinum compound to be used as a flame retardant additive is that disclosed in U.S. Pat. No. 3,814,730 of Karstedt. Generally speaking, this type of platinum complex is formed by reacting chloroplatinic acid containing 4 molecules of water of hydration with tetramethyl-tetravinylcyclotetrasiloxane in the presence of sodium bicarbonate in an ethanol solution.

As is known in the art, the SiH-olefin addition reaction coupling components (1) and (2) can take place at room temperature but is accelerated by higher temperatures. When the catalyst described in the U.S. patent of Karstedt is employed catalyst levels can go as low as 0.1 parts per million of platinum present in a mixture. When it is desired to speed up the cure such as in high speed encapsulation of electronic parts the levels of platinum are increased up to a maximum of about 25 ppm. The catalyst levels employed in various situations are, of course, a matter within the ordinary skill in the art depending upon the pot life desired and the snap-over or cure time desired. The compositions of the present invention may also be varied by the incorporation of various extenders or fillers.

Illustrative of the many fillers which can be employed are titanium dioxide, lithopone, zinc oxide, zirconium silicate, silica aerogel, iron oxide, diatomaceous earth, calcium carbonate, fumed silica, silazane treated silica, pecipitated silica, glass fibers, magnesium oxide, chromic oxide, zirconium oxide, aluminum oxide, alpha quartz, calcined clay, asbestos, carbon, graphite, cork, cotton, synthetic fibers, etc.

The preferred fillers which can be used in the practice of the present invention are the microsphere or microballoon type fillers. These fillers are characterized by being very small in size and consisting of gas filled spheres of glass or plastic. Finely crushed fly ash having closed pores may also be employed. It is preferred that these microsphere fillers have a diameter of from about 20 microns to about 250 microns and employed in amounts of from about 1 part to about 25 and preferably 14 parts per 100 parts of (1) and (2).

When a low viscosity polysiloxane mix is employed it is often necessary to add a filler in addition to the microsphere filler to increase the viscosity to the point where the microsphere filler will not separate from the polysiloxane prior to cure. Therefore, when the viscosity of the polysiloxane mix of (1) and (2) is below 5000 centipoises, from 0.5 to 5.0 parts of non-cellular filler are added to thicken the polysiloxane to the point where the lightweight cellular filler will not separate from the mix during cure or shelf standing. The application of the gels of the present invention is not difficult and is within the skill of the art. For example, artificial implantable breasts are prepared by filling a silicone rubber form with the gellable composition and then curing it. Orthopedic bed pads are produced by curing the gellable composition and then covering it with an elastomeric cover.

In addition to the above fillers, there may also be utilized a non-reaction diorganopolysiloxane where the organo groups are lower alkyl of 1 to 8 carbon atoms having a viscosity of 1,000 to 100,000 centipoise at 25° C at a concentration of 1 to 25 parts per 100 parts of (1) and (2). This non-reaction filler fluid or diluent allows the gel to be prepared at lower costs without detracting from the ultimate properties of the final gel. The most preferred diorganopolysiloxane for this purpose is a dimethylpolysiloxane of 1,000 to 20,000 centipoise viscosity at 25° C.

In addition, it is not always possible with general manufacturing procedures to produce a specific vinylpolysiloxane of (1) and the hydrogenpolysiloxane (2) that have the necessary hydride to vinyl ratios set forth above. Accordingly, in most cases it may be necessary to add to the reaction mixture a vinyl diluent which may have $ViMe_2SiO_{0.5}$ units or ViMeSiO units or both with the rest of the units being methylsiloxy units as is necessary and wherein the vinyl diluent has a viscosity in the range of 1,000 to 20,000 centipoise at 25° C. Such a vinyl diluent can be utilized at a concentration of 0.01 to 20 parts per 100 parts of fluid of (1) and (2) and desirably has a vinyl content of 0.01 to 5 mole percent and preferably 0.1 to 3 mole percent. It is only necessary that in the concentration of fluid (1) and the vinyl diluent that there be at least one vinyl siloxy unit for every silicon-bonded hydrogen atom in (2).

The friction loss due to fluids flowing through pipes is decreased by coating the insides of the pipes with the gellable composition and curing it. The friction of ships passing through water is decreased by coating the hulls of the ship with the gellable composition and curing it. The same curing technique is employed in filling tubes containing electrical conductors with the gellable composition. The same technique can be used in the manufacture of collision pads in cars, the manufacture of shock absorbing bumpers for cars, and the lining of crash helmets. Lightweight mattresses and pads are manufactured by using the gellable composition which has been filled with microballoons.

As illustrative of the best mode of the practicing of the invention, the following examples are set forth.

EXAMPLE 1

A mixture was prepared containing 100 parts of a methylvinylpolysiloxane having a viscosity of 2000 centipoises at 25° C consisting essentially of the following units. 98.39 mole percent $Me_2SiO$, 0.94 mole percent $ViMe_2SiO_{0.5}$, 0.52 mole percent MeViSiO and 0.15 mole percent $(Me)_3SiO_{0.5}$. This was mixed with 8.2 parts of a diluent copolymer containing 98.3 mole percent of $Me_2SiO$ units and 1.7 mole percent of $ViMe_2SiO_{0.5}$ units and 1.8 parts of a hydrogen siloxane containing 81.0 mole percent $Me_2SiO$ units, 17.0 mole percent MeHSiO units, and 2.0 mole percent $Me_2HSiO_{0.5}$ units. viscosity of the hydrogen siloxane material was less than 5000 centipoises at 25° C. To this composition was added sufficient catalyst described in Example 1 of the above-mentioned Lamoreaux patent to provide 10 ppm platinum based upon the weight of the vinyl-containing polysiloxane.

The three components were thoroughly mixed and used to encapsulate electrical components on an assembly line. The composition cured to a gel in 10 seconds at 125° C.

EXAMPLE 2

This example illustrates the versatility one can achieve with a single vinyl-containing polysiloxane. the 100 parts of vinyl-containing polysiloxane used in Example 2 is the same as that used in Example 1. The hydrogen containing siloxane was different from that used in Example 1 and the product which is formed was used to manufacture a high tear strength gel filled orthopedic mattress. The 2.5 parts of hydrogen containing polysiloxane in this Example 2, contained 77.2 mole percent $Me_2SiO$ units, 13.7 mole percent MeHSiO units and 9.1 mole percent $Me_3SiO_{0.5}$ units. The viscosity of this material was 50 centipoises at 25° C. The catalyst used was the same used in Example 1 at the same concentration. The 7.5 parts of diluent contained 99.2 mole percent $Me_2SiO$ units, 1.2 mole percent MeViSiO units and 2.6 mole percent $Me_3SiO$ units.

The mixture of components was stable, that is, it did not cure for 2 days standing at room temperature. It was used to fill elastic transparent mattress covers to form orthopedic pads which performed well. The strength of the material was determined by casting $8 \times 8 \times 1$ inch pads curing them at 125° C for 60 minutes and then placing a 12 lb. cylindrical weight 6 inches long on the pad. The tear strength of the pad is sufficient to hold body weights of individuals if the pad does not tear with the weight setting on it for a period of 72 hours. The gel pads of the present invention had more than sufficient strength to meet this requirement.

EXAMPLE 3

A lightweight orthopedic gel pad which was used in the manufacture of a mattress was made in the following manner. The 100 parts of vinyl-containing polysiloxane used in this Example 3, is the same as that used in Examples 1 and 2. The hydrogen-containing siloxane was the same as that used in Example 2 but only 2.0 parts were employed. The same diluent was used in this example as was used in Example 2, but 8.0 parts were employed. The catalyst used was the same as that of Example 2 and in the same concentration. The mixture was thickened with 2 parts of a fumed silica having a surface area of 200 square meters per gram and 14 parts of 50 micro and microspheres were added and the mixture was made homogeneous. The mixture was cured as in Example 2 providing a relatively lightweight mattress. The density of the microsphere containing gel was 0.67 grams per cubic centimeter.

I claim:

1. A reaction product silicone gel of a mixture comprising reacting (1) an organosiloxane having a viscosity of from 10 to 10,000 centistokes at 25° C, and being a copolymer consisting essentially of units of the formula $R_2ViSiO_{0.5}$, RViSiO, $R_2SiO$ and $MeR_2SiO_{0.5}$, where each R is individually selected from the group consisting of methyl and phenyl radicals and Vi represents a vinyl radical, at least 0.50 molar percent of the units in said copolymer being $R_2ViSiO_{0.5}$ units and RViSiO units where the terminal groups are at least 50 mole percent $ViR_2SiO_{0.5}$ units and may have as the rest of the total terminal units $MeR_2SiO_{0.5}$ units, (2) a liquid hydrogen siloxane of the average general formula XRMeSiO$(R_2SiO)_n$(RHSiO)$_m$SiMeRX, where each R is as above defined and X is selected from the group consisting of H and R, no more than 25 molar percent of the total R radicals present in (1) and (2) being phenyl, and $n$ and $m$ have such average values that the viscosity of the hydrogen siloxane is no more than 10,000 centistokes at 25° C and $m$ is at least 1, in the presence of a platinum or platinum compound catalyst in an amount sufficient to furnish at least 0.1 part per million of platinum based upon the combined weights of (1) and (2); the properties of (1) and (2) being such that prior to reaction there is an average of from 1.4 to 1.8 gram atoms of the silicon-bonded hydrogen atoms in (2) per gram molecular weight of (1) and there being at least one vinyl siloxy unit in (1) for every silicon-bonded hydrogen atom in (2), the molecular weight of (1) being calculated by the equation:

$$\log \text{visc.} = 1.00 + 0.0123 M^{.5}$$

where M is the molecular weight and "visc." is the viscosity of (1) in centistokes at 25° C.

2. The composition of claim 1 further characterized by the presence of from about 1 part to about 25 parts per 100 parts of (1) and (2) of gas filled microspheres having a diameter of from about 20 microns to about 250 microns.

3. The composition of claim 2 further characterized by the presence of from 0.5 to 5.0 parts of a non-cellular filler being present.

4. The composition of claim 1 further characterized by R being methyl and phenyl.

5. The composition of claim 1 further characterized by the viscosity of the hydrogen siloxane being from 1 to 1000 centistokes.

6. The composition of claim 1 further characterized by the platinum compound being formed by reacting chloroplatinic acid with a vinyl containing siloxane in the presence of sodium bicarbonate in an ethanol solution.

7. The composition of claim 1 further characterized by the platinum compound being a platinum vinylsiloxane complex.

8. The composition of claim 1 wherein there is present at a concentration of 1 to 25 parts of a diorganopolysiloxane diluent of 1,000 to 100,000 centipoise viscosity at 25° C, and where the organo groups are lower alkyl of 1 to 8 carbon atoms.

9. The composition of claim 1 wherein there is present from 0.01 to 20 parts of vinyl polysiloxane diluent of 1,000 to 20,000 centipose viscosity at 25° C, wherein the diluent has ViMe$_2$SiO$_{0.5}$ units or ViMeSiO units or both with the rest of the units being methylsiloxy units as is necessary and the vinyl diluent having a vinyl concentration such that in the combination of the organopolysiloxane (1) and the vinyl diluent there is at least one vinylsiloxy unit for every silicon-bonded hydrogen atom in (2).

10. A process for forming a silicone gel comprising reacting (1) an organosiloxane having a viscosity of from 10 to 10,000 centistokes at 25° C, and being a copolymer consisting essentially of units of the formula R$_2$ViSiO$_{0.5}$, RViSiO, R$_2$SiO and MeR$_2$SiO$_{0.5}$, where each R is individually selected from the group consisting of methyl and phenyl radicals and Vi represents a vinyl radical, at least 0.50 molar percent of the units in said copolymer being R$_2$ViSiO$_{0.5}$ units and RViSiO units where the terminal groups are at least 50 mole percent ViR$_2$SiO$_{0.5}$ units and may have as the rest of the total terminal units MeR$_2$SiO$_{0.5}$ units, (2) a liquid hydrogen siloxane of the average general formula, XRMeSiO$(R_2SiO)_n$(RHSiO)$_m$SiMeRX, where each R is as above defined and X is selected from the group consisting of H and R, no more than 25 molar percent of the total R radicals present in (1) and (2) being phenyl, and $n$ and $m$ have such average values that the viscosity of the hydrogen siloxane is no more than 10,000 centistokes at 25° C and $m$ is at least 1, in the presence of a platinum or platinum compound catalyst in an amount sufficient to furnish at least 0.1 part per million of platinum based upon the combined weights of (1) and (2), the properties of (1) and (2) being such that prior to reaction there is an average of from 1.4 to 1.8 gram atoms of the silicon-bonded hydrogen atoms in (2) per gram molecular weight of (1) and there being at least one vinyl siloxy unit in (1) for every silicon-bonded hydrogen atom in (2), the molecular weight of (1) being calculated by the equation:

$$\log \text{visc.} = 1.00 + 0.0123 M^{.5}$$

where M is the molecular weight and "visc." is the viscosity of (1) in centistokes at 25° C.

11. The process of claim 10 further comprising adding to the reaction mixture from about 1 part to about 25 parts per 100 parts of (1) and (2) of gas filled microspheres having a diameter of from about 20 microns to about 250 microns.

12. The process of claim 10 further comprising adding to the reaction mixture from 0.5 to 5.0 parts of a non-cellular filler being present.

13. The process of claim 10 wherein R is methyl and phenyl.

14. The process of claim 10 wherein the viscosity of the hydrogen siloxane being from 1 to 1000 centistokes.

15. The process of claim 10 wherein the platinum compound is formed by reacting chloroplatinic acid with a vinyl-containing siloxane in the presence of sodium in an ethanol solution.

16. The process of claim 10 wherein the platinum compound is a platinum vinylsiloxane complex.

17. The process of claim 10 wherein there is further added to the reaction mixture at a concentration of 1 to 25 parts a diorganopolysiloxane diluent of 1,000 to 100,000 centipoise viscosity at 25° C and where the organo groups are lower alkyl of 1 to 8 carbon atoms.

18. The process of claim 10 wherein there is further added to the reaction mixture from 0.01 to 20 parts of vinyl polysiloxane diluent of 1,000 to 20,000 centipoise viscosity at 25° C wherein the diluent has ViMe$_2$SiO$_{0.5}$ units or ViMeSiO units or both with the rest of the units being methylsiloxy units as is necessary and the vinyl diluent having a vinyl concentration such that in the combination of the organopolysiloxane (1) and the vinyl diluent there is at least one vinylsiloxy unit for every silicon-bonded hydrogen atom in (2).

* * * * *